US008529637B2

(12) United States Patent
Vohra et al.

(10) Patent No.: US 8,529,637 B2
(45) Date of Patent: Sep. 10, 2013

(54) FOAM OXIDATIVE HAIR COLORANT COMPOSITION WITH THE FREE-BASE OF 1,4-DIAMINO-2-METHOXYMETHYL BENZENE

(71) Applicant: The Procter & Gamble Company, Cincinnati, OH (US)

(72) Inventors: Firoj Vohra, Deerfield Township, OH (US); Sebastian Karol Galazka, Loveland, OH (US); Christopher Gerald Donner, Liberty Township, OH (US); George Scott Kerr, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/630,256

(22) Filed: Sep. 28, 2012

(65) Prior Publication Data

US 2013/0081647 A1 Apr. 4, 2013

Related U.S. Application Data

(60) Provisional application No. 61/541,378, filed on Sep. 30, 2011, provisional application No. 61/596,381, filed on Feb. 8, 2012.

(51) Int. Cl.
*A61Q 5/10* (2006.01)
(52) U.S. Cl.
USPC ................. 8/405; 8/406; 8/408; 8/410; 8/435

(58) Field of Classification Search
USPC .............................. 8/405, 406, 408, 410, 435
See application file for complete search history.

(56) References Cited

U.S. PATENT DOCUMENTS

| | | | |
|---|---|---|---|
| 2,273,564 | A | 2/1942 | Dickey |
| 3,578,387 | A | 5/1971 | Charles |
| 3,709,437 | A | 1/1973 | Wright |
| 3,937,364 | A | 2/1976 | Wright |
| 3,977,826 | A | 8/1976 | Iscowitz |
| 4,022,351 | A | 5/1977 | Wright |
| 4,147,306 | A | 4/1979 | Bennett |
| 4,184,615 | A | 1/1980 | Wright |
| 4,615,467 | A | 10/1986 | Grogan |

(Continued)

FOREIGN PATENT DOCUMENTS

| | | |
|---|---|---|
| DE | 3731202 A1 | 7/1989 |
| EP | 1 142 563 A1 | 10/2001 |

(Continued)

OTHER PUBLICATIONS

Leung, A Y, "Encyclopedia of Common Natural Ingredients Used in Food, Drugs and Cosmetics (2d Edition)", Jan. 1, 1996, Wiley, NY, US, p. 446.

(Continued)

*Primary Examiner* — Eisa Elhilo
(74) *Attorney, Agent, or Firm* — James T. Fondriest

(57) ABSTRACT

An oxidative hair colorant composition to be dispensed from a manually-actuable, non-aerosol dispenser as a foam. The oxidative hair colorant composition contains the free-base of 1,4-diamino-2-methoxymethyl benzene to achieve for efficient dye precursor levels in formulation and to achieve a desire rheology profile of the oxidative hair colorant composition.

18 Claims, 5 Drawing Sheets

(56) References Cited

U.S. PATENT DOCUMENTS

| | | | |
|---|---|---|---|
| 4,796,812 | A | 1/1989 | Grollier |
| 4,921,170 | A | 5/1990 | Grollier |
| 4,997,451 | A | 3/1991 | Clausen |
| 5,443,569 | A | 8/1995 | Uehira |
| 6,106,578 | A | 8/2000 | Jones |
| 6,604,693 | B2 | 8/2003 | Santagiuliana |
| 6,648,923 | B1 * | 11/2003 | Goettel et al. ............ 8/405 |
| 6,835,210 | B1 | 12/2004 | Bartolone |
| 7,040,507 | B2 | 5/2006 | Koike |
| 7,445,645 | B2 | 11/2008 | Sabelle |
| 7,850,049 | B2 | 12/2010 | Ciavarella |
| 7,955,400 | B2 | 6/2011 | Fujinuma |
| 8,025,702 | B2 | 9/2011 | Fujinuma |
| 8,025,703 | B2 | 9/2011 | Ogawa |
| 2002/0058017 | A1 | 5/2002 | Tajima |
| 2003/0180238 | A1 | 9/2003 | Sakurai |
| 2003/0192133 | A1 | 10/2003 | Matsuo |
| 2004/0213752 | A1 | 10/2004 | Fujinuma |
| 2004/0254253 | A1 | 12/2004 | Culeron |
| 2005/0222001 | A1 | 10/2005 | Baumeister |
| 2005/0226824 | A1 | 10/2005 | Kawa |
| 2006/0054634 | A1 | 3/2006 | Mekata |
| 2006/0207037 | A1 | 9/2006 | Fadel |
| 2006/0219738 | A1 | 10/2006 | Ilzuka |
| 2008/0087293 | A1 | 4/2008 | Glenn |
| 2010/0126522 | A1 | 5/2010 | Fujinuma |
| 2010/0126523 | A1 | 5/2010 | Fujinuma |
| 2010/0236570 | A1 | 9/2010 | Fujinuma |
| 2010/0242187 | A1 | 9/2010 | Miyabe |
| 2010/0251488 | A1 | 10/2010 | Fujinuma |
| 2010/0257677 | A1 | 10/2010 | Miyabe |
| 2010/0299848 | A1 | 12/2010 | Fujinuma |
| 2010/0313905 | A1 | 12/2010 | Fujinuma |
| 2010/0316583 | A1 | 12/2010 | Fujinuma |
| 2011/0073128 | A1 | 3/2011 | Ogawa |
| 2011/0214682 | A1 | 9/2011 | Fujinuma |
| 2011/0284421 | A1 | 11/2011 | Lane |
| 2011/0284584 | A1 | 11/2011 | Velazquez |
| 2011/0284586 | A1 | 11/2011 | Kerr |
| 2011/0284587 | A1 | 11/2011 | Galazka |
| 2012/0078016 | A1 | 3/2012 | Gardlik |
| 2012/0130128 | A1 | 5/2012 | Goettel |

FOREIGN PATENT DOCUMENTS

| | | |
|---|---|---|
| EP | 1765267 B1 | 5/2005 |
| FR | 2604622 | 12/1990 |
| JP | 2007-291015 A | 11/2007 |
| JP | 2007-291016 A | 11/2007 |
| JP | 2007-314523 A | 12/2007 |
| JP | 2007-314524 A | 12/2007 |
| JP | 2009-149322 A | 7/2009 |
| JP | 2009-149323 A | 7/2009 |
| JP | 2009-149324 A | 7/2009 |
| JP | 2009-149325 A | 7/2009 |
| JP | 2009-149326 A | 7/2009 |
| JP | 2009-149327 A | 7/2009 |
| JP | 2010-006804 A | 1/2010 |
| JP | 2010-006805 A | 1/2010 |
| WO | WO 91/14759 | 10/1991 |
| WO | WO 97/13585 | 4/1997 |
| WO | WO 2009/130461 | 10/2009 |
| WO | WO 2010/106789 | 9/2010 |

OTHER PUBLICATIONS

*Finkelstein Reaction*; Wikipedia summary, 2 pages.

Dorretijn; *The Reactivity of o-Hydroxybenzyl Alcohol and Derivatives in Solution at Elevated Temperatures*; J. Org. Che.m. 1999, 64, 3012-3018.

Rondestvedt; *Meth-Terminated Perfluoroalkyl Iodides and Related Compounds*; J. Org. Chem., vol. 42, No. 11, 1977, 1985-1990.

Silk; *The Snythesis of 3-Chloro-4-nitro- and 4-Amino-3-chlorobenzyl Alcohols*; 7 pgs.

* cited by examiner

FOAM OXIDATIVE HAIR COLORANT COMPOSITION WITH THE FREE-BASE OF 1,4-DIAMINO-2-METHOXYMETHYL BENZENE

FIELD OF THE INVENTION

The present invention relates to oxidative hair colorant compositions for use in combination with a foaming dispenser such that a desired foam hair colorant product is produced.

BACKGROUND OF THE INVENTION

An outstanding issue with respect to hair colorants includes ease of application and concerns over messy application resulting in skin staining and uneven hair color results. Recent trends indicate that consumers find handling of foamed products preferable to gels, creams or liquids.

A way to generate a foam product is via a non-pressurized dispenser in the form of a pump foamer or squeeze foamer. The non-pressurized dispensers can be difficult to utilize with hair colorant composition due to the rheology limitations on such systems. As a user supplies the force needed to dispense the product repeatedly, the rheology must be kept to a range that allows for ease of repeated dispensing without fatigue of the user's hands while still providing an acceptable foamed product.

Oxidative hair colorant compositions utilizes dye precursors that are in the form of salts, the first portion of the salt provides the chromophore precursor while the second portion of the salt is a cation or anion. The second portion does not contribute to the chromophore formation.

The formulation window, or available volume, for dye precursors becomes relatively limited when large amounts of dye precursors are needed to achieve the desired end color for the hair, such as brown and black end hair colors. Therefore, it would be a benefit to control the amount of the second portion of the dye precursor through the use of an oxidation-insensitive free base dye precursor. An oxidation-insensitive free base dye precursor would eliminate the second portion of a traditional salt, the second portion not contributing to the chromophore formation. The amount of dye precursor can be increased within the formulation window of the hair colorant composition with the elimination of a cation or anion that does not contribute to the chromophore formation.

It is known that salt content affects the rheology profile by increasing mixed viscosity when salt levels are relatively lower and decreasing mixed viscosity when salt levels are relatively higher. So while more efficient dye precursor loading in the formulation window results from reducing the second portion of the dye precursors allows for, it also results in a hair colorant composition mixed viscosity that is too difficult to dispense through a manually-actuable, non-aerosol dispenser.

Nevertheless such foam oxidative hair colourant compositions must continue to meet consumer expectations with regard to the overall consumer application experience and overall colour result. In particular such products need to be easy and quick to apply and use, deliver only low levels of skin staining and deliver the anticipated overall colour result which is maintained over the subsequent wash cycles. Moreover, the foam must be readily generated and expelled from the dispenser with only minimal foam generation within the dispenser itself and have sufficient durability to be applied onto the hair prior to collapse upon massaging to ensure complete distribution over the entire head of hair.

It has been found that having a particular rheological profile of the oxidative hair coloring composition reduces messy application issues and allows for ease in dispensing while still allowing for an efficient dye precursor loading into the hair colorant composition.

SUMMARY OF THE INVENTION

The present application relates to an oxidative hair colorant product comprising an oxidative hair colorant composition comprising from about 0.1 wt % to about 10 wt % by weight of the oxidative hair colorant composition of a free-base of 1,4-diamino-2-methoxymethyl benzene; an alkalizing agent; a solvent; an oxidizing agent; a foaming agent; and a salt; and a manually-actuable, non-aerosol dispenser and wherein the oxidative hair colorant composition has a high shear viscosity of less than 200 mPa·s and a low shear (mixed) viscosity of between 10 mPa·s and 500 mPa·s.

The present application further relates to an oxidative hair colorant composition comprising from about 0.1 wt % to about 10 wt % by weight of the oxidative hair colorant composition of a free-base of 1,4-diamino-2-methoxymethyl benzene; an alkalizing agent; a solvent; an oxidizing agent; a foaming agent; and a salt; wherein the oxidative hair colorant composition has a high shear viscosity of is less than 200 mPa·s and a low shear (mixed) viscosity of between 10 mPa·s and 500 mPa·s.

The present application further relates to a kit comprising components to form an oxidative hair colorant composition, the kit comprising: a tint composition component comprising a solvent, a free-base of 1,4-diamino-2-methoxymethyl benzene and at least one other dye precursor, a salt and an alkalizing agent; a developer composition component comprising an oxidizing agent; and a manually-actuable, non-aerosol dispenser.

BRIEF DESCRIPTION OF THE DRAWINGS

FIG. 1A is a magnified view, taken along lines 1A-1A of FIG. 1, of a mesh disposed near a diffuser opening or mixing chamber egress orifice of the dispenser;

FIG. 1B is a magnified view, taken along lines 1B-1B of FIG. 1, of a mesh, disposed near a dispenser head orifice;

FIG. 3A is a magnified view, taken along lines 3A-3A of FIG. 3, of a mesh disposed near a diffuser opening or mixing chamber egress orifice of the dispenser;

FIG. 3B is a magnified view, taken along lines 3B-3B of FIG. 3, of a mesh, disposed near a dispenser head orifice.

DETAILED DESCRIPTION OF THE INVENTION

Figure 1:
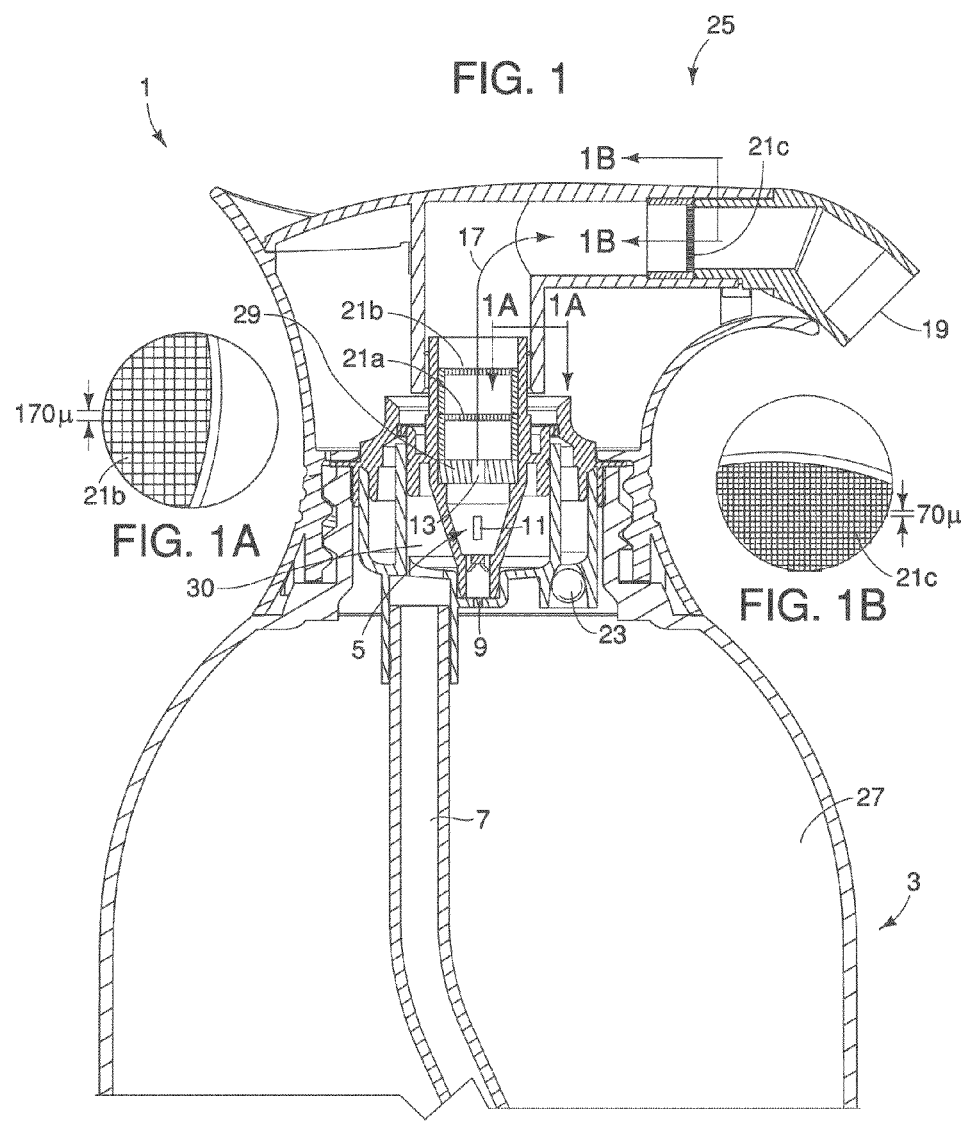
FIG. 1 illustrates an embodiment of the manually-actuable, non-aerosol dispenser cross sectional view.
Figure 2:
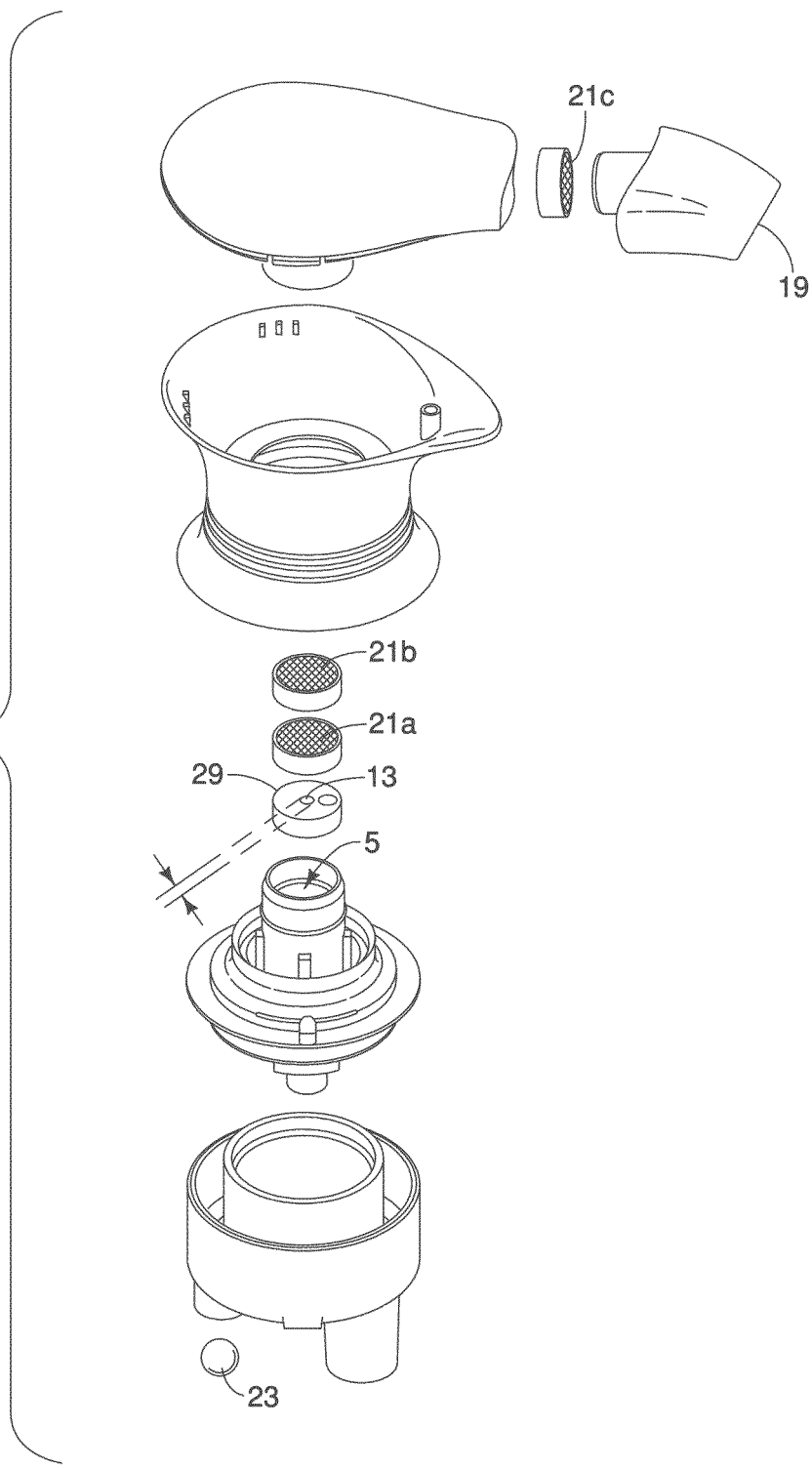
FIG. 2 is an exploded view of a dispenser head of the dispenser of FIG. 1.

The oxidative hair colorant product utilizes a manually-actuable, non-aerosol dispenser, such as a squeeze foamer or a pump foamer, to form a foamed oxidative hair colorant. The oxidative hair colorant composition is a shear-thinning composition that comprises a mixed viscosity of the oxidative hair colorant composition that allows for ease in dispensing from the manually-actuable, non-aerosol dispenser.

The oxidative hair colorant composition may be formed through the combination of two or more subcomponents such as a tint composition and a developer composition. The components of the oxidative hair colorant composition or subcomponents thereof, combine together to make 100% of the oxidative hair colorant composition or subcomponent thereof. A percentage of the 100% is dedicated to dye precursors otherwise known as primaries and couplers along with other components such as solvents, alkaline agents and oxidizing agents. The percentage of dye precursors is often a "window" that can be populated with one or more dye precursors. This window becomes crowded when darker shades are desired as the amount and number of dye precursors increases. With the increase in the amount and number, the amount of corresponding salt ion with the dye precursor increases as well in the window. Therefore, it would be advantageous to have less corresponding salt ion enter into the window such that more dye precursor can be present in the window.

1,4-diamino-2-methoxymethyl Benzene

The oxidative hair coloring composition or tint composition of the oxidative hair colorant product comprises a primary that is the free-base of 1,4-diamino-2-methoxymethyl benzene.

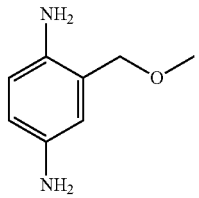

The free-base form of 1,4-diamino-2-methoxymethyl benzene is oxidation-insensitive and does not bring a corresponding salt ion into the formulation window for the hair colorant composition or the tint composition of the hair colorant product.

The oxidative hair colorant composition or the tint composition may comprise from about 0.1 wt % to about 10 wt % by weight of the tint composition, such as 1 wt % to 10 wt %, such as 2 wt % to 10 wt % of the tint composition of the free base form of 1,4-diamino-2-methoxymethyl benzene.

Alkalizing Agent

The oxidative hair colorant composition, generally in a tint composition, comprises an alkalizing agent.

Any alkalizing agent known in the art may be used such as: alkanolamines, for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol; guanidium salts; and alkali-metal and ammonium hydroxides and carbonates, such as sodium hydroxide and ammonium carbonate. A preferred alkalizing agent is monethanolamide. Particularly, preferred alkalizing agents are those which provide a source of ammonium ions.

Any source of ammonium ions is suitable for use herein. Preferred sources of ammonium ions include ammonium chloride, ammonium sulfate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia, ammonium hydroxide and mixtures thereof.

The oxidative hair colorant composition or the tint composition may comprise from about 0.1% to about 10% by weight, such as from about 0.5% to about 5%, such as from about 1% to about 3% of an alkalizing agent.

Solvent

The oxidative hair colorant composition may comprise solvents such as water, lower aliphatic alcohols, for example aliphatic alcohols with from 1 to 4 carbon atoms such as ethanol, propanol and isopropanol, or glycols such as glycerin and 1,2-propylene glycol. The solvents may be utilized for the oxidative hair colorant composition or in sub-components such as the tint composition or developer composition in concentrations of from 0.1 to 30%, from 1 to 30%, from 5 to 30% and from 10 to 30% by weight.

Oxidizing Agent

The oxidative hair colorant compositions herein, generally in the developer composition, may comprise at least one source of an oxidizing agent. Preferred oxidizing agents for use herein are water-soluble peroxygen oxidizing agents. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can also be used if desired. The oxidizing agents may be provided in aqueous solution or as a powder which is dissolved prior to use. Preferred for use in the compositions according to the present invention are hydrogen peroxide, percarbonate, persulphates and combinations thereof.

The oxidizing agent may comprise from about 0.1% to about 40% by weight, from about 1% to about 30% by weight, and from about 2% to about 30% by weight of the oxidative hair colorant composition or developer composition.

Another potential oxidizing agent for use herein is a source of peroxymonocarbonate ions. Preferably such a source is formed in situ from a source of hydrogen peroxide and a hydrogen carbonate ion source. Such an oxidizing agent has been found to be particularly effective at a pH of up to and including 9.5, preferably 7.5 to 9.5 more preferably about pH 9. Moreover, this system is also particularly effective in combination with a source of ammonia or ammonium ions. See U.S. Pat. No. 7,204,861, col. 6, line 14-col. 7, line 5.

Foaming Agent

Surfactants are widely used in oxidative hair colorant compositions as homogenizing agents and in the case of foam hair colorants, surfactants are used as foam stabilizing agents. When surfactants are used in foam hair colorants, they may be present in an amount of from 0.1% to 20%, preferably from 0.1% to 10% by weight of the composition to be dispensed, typically exemplified in amounts of at least 1.9% by weight.

The foaming agent may be anything so long as the foaming agent has foaming properties including surfactants such as nonionic, anionic, cationic and amphoteric surfactants. Preferred foaming agents include amphoteric surfactants. Useful surfactants are discussed in US 2004/0213752 in paragraphs [0024]-[0027].

Useful anionic surfactants include alkyl ether carboxylates, alkyl ether sulphates, alkyl glyceryl sulphonates, alkylamido ether sulphates, alkylarylpolyether sulphates, alkyl monoglyceride sulphates, alkyl ether sulphonates, alkylamide sulphonates; alkyl succinates, alkyl sulphosuccinates, alkyl ether sulphosuccinates, alkylamide sulphosuccinates; alkyl sulphosuccinamates; alkyl sulphoacetates; alkyl ether phosphates; acyl sarcosinates, N-acyl methylaminopropionate; acyl isethionates, N-acyltaurates; acyl lactylates; carboxyalkyl ether of alkyl polyglucosides; alkyl lecithin derivatives. In one embodiment, an anionic surfactant is selected as C8-C30 alkyl ether phosphates having from 1 to 20, preferably 2 to 10 ethylene oxide units, and a non-ionic surfactant selected from polyoxyethylene alkyl ethers having at least 25, preferably from 100 to 200 ethylene oxide units.

Useful nonionic surfactants includes one or more polyethyleneoxide chains include the following compounds: polyoxyethylene alkyl ethers, polyethyleneglycol fatty acid esters, polyoxyethylene castor oil, polyoxyethylene hydrogenated castor oil, polyoxyethylene fatty amides and their momoethanolamine and diethanolamine derivatives and polyethoxylated fatty amines. In one embodiment include polyoxyethylene alkyl ethers or polyethylene glycol fatty acid esters having at least about 25, preferably from about 50 to 200, most preferably from about 100 to 200 ethylene oxide units, for example ceteareth-25, steareth-100, steareth-150 and steareth-200.

It has been found that the use of surfactant in oxidative hair colorant compositions may contribute to the formation of bubble in the reservoir of a dispenser when the compositions are subject to agitation, e.g. vigorous shaking. In one embodiment, the oxidative hair colorant compositions do not require the presence of a surfactant to create and maintain foam of acceptable quality. While small amounts of surfactant may be present as process aids, e.g. to assist homogenization of some components, or a function other than foaming, in this embodiment, the compositions may be substantially free of surfactant.

As used herein "substantially free of surfactant" means that no anionic, cationic or amphoteric surfactant is purposefully added to the composition. In one embodiment, the composition is substantially free of anionic, cationic, amphoteric and nonionic surfactants.

Surfactants may be present in trace amounts due to presence in components, such as polymers which may require surfactant for stabilization of the polymer during storage or is present due to the polymerization process to make the polymer. By "trace amounts" it is intended that the levels of surfactant are less than 500 ppm, such as 0 ppm to 500 ppm, less than 200 ppm, such as between 0 ppm and 200 ppm and less than 100 ppm, such as between 0 ppm and 100 ppm. In general the compositions will contain less than 0.05% by weight, preferably less than 0.02% by weight, more preferably less than 0.01% by weight based on the oxidative hair colorant composition to be dispensed of surfactant.

It has been found that certain materials, which are not surfactants, are capable of acting as foam stabilizing agents in oxidative hair colorant compositions and are included as foaming agents herein. As used herein "foam stabilizing agents" include not only components that can help to stabilize the liquid film of the foam bubbles, but components that may also generate foam. Therefore foaming agents are included in the meaning of foam stabilizing agents. These desired agents allow stable foams of the oxidative hair colorant composition to be formed and maintained for the desired timeframe of consumer usage.

Foam Formation and Stability

Foam consists of a dispersion of gas bubbles in a liquid. Bubbles of gas rupture on contact with each other and additives are needed to retard this contact. The bilayer films between two bubbles in foam are fairly flat surfaces while the surfaces at plateau borders where three bubbles meet are curved. There are known chemical-physical properties which slow down or even stop the film thinning process caused by drainage and stabilize the foam.

Foam Stabilizing Agents

The foam stabilizing agents used in the compositions of the invention are selected to provide foaming benefits and/or foam stabilization benefits and are stable in the presence of an oxidizing agent or in the presence of alkaline environments. The foam stabilizing agent may be present in a sub-component of the hair colorant composition, such as in a tint composition component or in a developer composition component.

Suitable foam stabilizing agents include polymeric foam stabilizers and polymeric emulsifiers. Combinations of polymeric emulsifiers and polymeric foam stabilizers are also embodied herein. Polymeric foam stabilizers may be used at levels of from about 4% to about 20%.

Polymeric Foam Stabilizers

Polymeric foam stabilizing agents suitable for use herein include cellulose materials such as methylcellulose, hydroxypropyl methylcellulose (sold as METHOCEL 40-101 and methylcellulose sold as METHOCEL A4MP) and ethylcellulose (Cecetyl hydroxyethylcellulose sold as NATROSOL PLUS) and mixtures thereof.

The hydroxypropyl methylcellulose may have the general structure of:

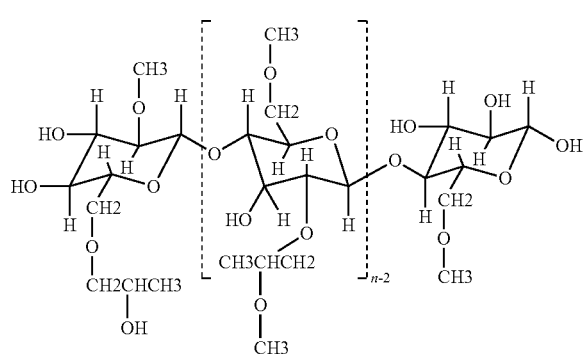

The methylcellulose may have the general structure of:

The "n" of these structures is selected to give the desired viscosity of the methylcellulose material. The METHOCEL 40-101 has a viscosity of about 75,000 mPa s (for a 2% aqueous solution at 20° C. with a Ubbelohde tube viscometer) and the METHOCEL A4MP has a viscosity of about 4000-5000 mPa s (for a 2% aqueous solution at 20° C. with a Ubbelohde tube viscometer).

Another suitable foam stabilizing agent includes (meth) acrylic polymers such as an acrylate/$C_{10\text{-}30}$ alkyl acrylate crosspolymer, a copolymer of $C_{10\text{-}30}$ alkyl acrylates and one or more monomers of acrylic acid, methacrylic acid or one of their simple esters crosslinked with an allyl ether of sucrose or an allyl ether of pentaerythritol. It is commercially available from Goodrich as PEMULEN TR-1 and PEMULEN TR-2. PEMULEN TR-1 polymer is preferred. CAPIGEL 98, an acrylates copolymer produced by SEPPIC is also suitable.

Another suitable foam stabilizing agent for use herein is a hydrophobically-modified alkali soluble emulsion polymer synthesized through an emulsion polymerization process from an acid/acrylate copolymer backbone and a monomer that connects hydrophobic groups as side chains. An example of such a material is ACULYN™ 22, commercially available from Rohm Haas with an INCI name of Acrylates/Steareth-20 Methacrylate Copolymer.

Another suitable foam stabilizing agent includes anionic alkali-soluble polymer emulsion synthesized from acid and acrylate co-monomers through emulsion polymerization. An example of such a material is ACULYN™ 33, commercially available from Rohm Haas with an INCI name of Acrylates Copolymer.

Mixtures of ACULYN™ 22 and ACULYN™ 33 may be used. One embodiment utilizes a mixture of ACULYN™ 22 and ACULYN™ 33 in a ratio (weight) of 1:2 to 1:5 weight ratio based upon the weight of the oxidative hair colorant composition or a sub-component such as a developer composition. In another embodiment, a mixture of ACULYN™ 22 and ACULYN™ 33 in a ratio (weight) of 1:3 to 1:5 by weight of the developer composition is utilized. In one embodiment, a mixture of ACULYN™ 22 and ACULYN™ 33 in a ratio (weight) of 1:3 to 1:4 by weight of the developer composition is utilized. In another embodiment, a mixture of ACULYN™ 22 and ACULYN™ 33 in a ratio (weight) of 4:1 to 1:1 by weight of the developer composition is utilized. In another embodiment, a mixture of ACULYN™ 22 and ACULYN™ 33 in a ratio (weight) of 3:1 to 2:1 by weight of the developer composition is utilized.

Polyquaternium-55, a polymer comprising vinyl pyrrolidone (VP), dimethylaminopropyl methacrylamide (DMAPA) and methacryoylaminopropyl lauryldimonium chloride (MAPLAC) is also suitable for use herein and has the following generalized structure:

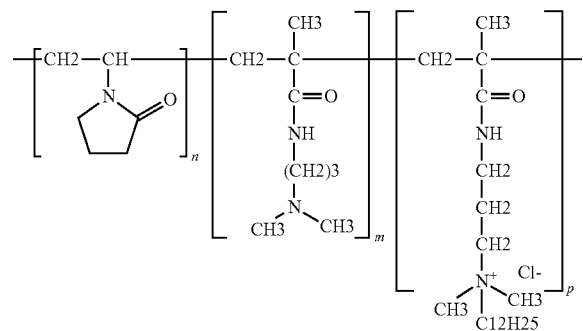

Polyquaternium-55 is sold under the tradename STYLEZE® in a 10 and 20 variation. The n, m and p levels depend on the monomer ratio. The STYLEZE®-10 has a monomer ratio of 0.85VP:0.11DMAPA:0.4MAPLAC. The STYLEZE®-20 has a monomer ratio of 0.85 VP:0.11DMAPA:0.4MAPLAC.

Another suitable foam stabilizing agent includes a polyoxyethylene, polyoxypropylene block polymer that conforms generally to the formula shown below in which the average values of x, y and z are respectively 31, 54 and 31.

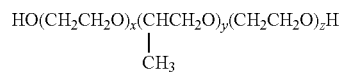

sold under the tradename POLOXAMER 334.

Another suitable foam stabilizing agent includes a polyethyleneoxide-polypropyleneoxide-polyethyleneoxide block polymer terminating in primary hydroxyl groups sold under the tradename PLURONIC P104 and PLURONIC F108 (ex. BASF).

Polymeric Emulsifiers

Suitable polymeric materials for use as a foam emulsifying agent include polysaccharides, cellulosic materials, amine-bearing polymers, polysiloxanes and mixtures thereof.

Suitable polysaccharides include xanthan gum, carrageenin gum, guar-guar, cationic guars, hydroxypropyl guar gum, agar-agar, locust bean gum, alginates, tyloses, salts of any of these materials (such as sodium salts) and mixtures thereof.

Suitable cellulosic materials include cellulose ethers, such as carboxymethylcellulose, ethylcellulose, hydroxypropylcellulose, methylcellulose, cellulose mixed ethers, such as carboxymethylhydroxyethylcellulose, ethylhydroxyethylcellulose, methoxyhydroxyalkylcelluloses, methylhydroxyalkylcelluloses, such as methylhydroxyethylcellulose, methylhydroxypropylcellulose, methylhydroxybutylcellulose; and mixtures of these.

Suitable amine-bearing polymers include deacytylated chitin, sometimes known as chitosan, which as been modified to be soluble in basic conditions usually by alkylation or by carboxymethylation, but other modifications of chitin are also suitable. See *Chitosan Derivatives Obtained By Chemical Modifications For Biomedical And Environmental Applications*; International Journal of Biological Macromolecules; Volume 43, Issue 5, 1 Dec. 2008, Pages 401-414.

Suitable polysiloxanes include dimethylpolysiloxanes, methylphenylpolysiloxanes, cyclic silicones as well as silicone compounds modified by amino, fatty acid, alcohol, polyether, epoxy, fluoro, glycoside and or alkyl groups. Preferred as silicone compounds according to the present invention are polysiloxane-polyether copolymers aka dimethicone copolyol, which are available from the company named Goldschmidt AG of Essen under the trade name ABIL®, especially polysiloxane-polyether copolymers of the B 88 product family, such as ABIL® B 8843, ABIL® B 8851, ABIL® B 8852, ABIL® B 8863, ABIL® B 88183 and ABIL® B 88184.

The foaming stabilizing agent is present in the oxidizing hair colorant composition to be dispensed in an amount sufficient to allow formation and/or stabilization of foam. In one embodiment, the foam stabilizing agent will be present in an amount of from 1 to 25% by weight, from 2 to 15% by weight and from 2 to 10% by weight of the oxidizing hair colorant composition.

In the case of a multi-part kit, the foam stabilizing agent may be present in one or more of the subcomponents. Preferably, the foam stabilizing agent is present in a subcomponent containing the oxidizing agent (developer) since a single developer composition may be used with a plurality of different hair dye (tint) formulations that form several different hair colors. The foam stabilizing agent may be present in the developer composition from 1 to 25% by weight, from 2 to 20% by weight, and from 5% to 20% by weight of the developer composition.

Salt

The formulation also comprises a salt to address any rheology needs, for example, if the resulting mixed viscosity is too high to use with a manually-actuable, non-aerosol dispenser. The use of a salt to reduce the mixed viscosity has been found to be easier than increasing the mixed viscosity through other means. The use of a free-base 1,4-diamino-2-methyoxymethyl benzene allows for an initial reduction of salt content allowing for a relatively higher mixed viscosity, which can then be reduced to work with a manually-actuable, non-aerosol dispenser by the inclusion of a salt.

Common and suitable salts may be used such a sodium chloride, potassium chloride, ammonium chloride, sodium sulfate, potassium sulfate, ammonium sulfate, sodium phosphate, potassium phosphate, ammonium phosphate and the like.

Rheology Profile

The oxidative hair colorant composition has a desired rheological profile during usage that ensures a desired user experience when in contact with the oxidative hair colorant composition. The composition of the present invention is subject to different stress/strain forces during the consumer's use of the formulation. The formulation is subject to mixing of two or more components together to form the desired oxidative hair colorant composition having a low shear (mixed) viscosity. The formulation is then foamed by passing it through the foaming means, such as a squeeze foaming engine and is expelled into a user's hand. The viscosity of the formulation as it is being passed through the foaming means should be shear thinning and may be described as a high shear viscosity. The formulation is then applied to the hair and the foam collapses and forms a liquid on the hair.

As used herein the terms "low shear viscosity" and "mixed viscosity" is the viscosity of the personal care composition prepared and measured by the methods defined below. In one embodiment, a hair colorant composition where two or more sub-components are mixed together, such as a sub-component comprising an oxidative dye precursor (tint composition) and a sub-component comprising an oxidizing agent (developer composition), by a consumer just prior to use of the composition, the low shear (mixed) viscosity would be the viscosity of the resulting mixture of the tint composition and developer composition rather than the viscosity of the individual sub-components prior to mixing together.

The low shear (mixed) viscosity of the oxidative hair colorant composition is from about 10 cps (0.01 pascal seconds) to about 500 cps (0.5 pascal seconds), from about 10 cps (0.01 pascal seconds) to about 450 cps (0.45 pascal seconds), from about 100 cps (0.1 pascal seconds) to about 450 cps (0.45 pascal seconds).

As used herein "high shear viscosity" means a composition is measured at a shear rate 500 $s^{-1}$ according to the method below. The high shear viscosity is believed to represent the viscosity of the oxidative hair colorant composition moving from the reservoir to the dispensing head orifice, usually through a foaming means such as the mixing chamber where high shear rates of air and liquid composition are used to form a foam.

The high shear viscosity of the oxidative hair colorant composition is less than 200 mPa s (200 cps), preferably less than 100 mPa s (100 cps), such as from about 1 mPa s (1 cps) to about 200 mPa s (200 cps). In one embodiment, the high shear viscosity of the oxidative hair colorant composition is between about 20 mPa s (20 cps) to about 100 mPa s (100 cps).

Foam

As used herein "foam" means an oxidative hair colorant composition which after being passed through a manually-actuable, non-aerosol dispenser has bubbles that sustain their shape and give a volume independent of any type of container. The foam preferably comprises a uniform bubble size. Preferably, the volume of the foam has a specific volume from about 6 ml/g to about 14 ml/g, such as about 7.5 ml/g to about 12 ml/g, more preferably from about 8 ml/g to about 10.5 ml/g immediately after dispensing.

The minimum time for the foam to maintain its volume immediately after dispensing is at least long enough to transfer from a user's hand to the desired location on the hair, e.g. the foam substantially maintains its shape and foam specific volume is for at least 10 seconds, for example at least 12, or at least 15 seconds. It could be longer if a quantity of foam, e.g. a bowl full by a hair dresser, is generated and spreading on the head only starts once the bowl full is readily made.

The collapse of the foam after being applied to desired location on the hair could be as quickly as 3 to 10 minutes but may be up to 15 minutes, or up to 30 minutes, or even up to an hour. It could even be longer if that was desired but should match the desired coloring experience to achieve an intended end result.

Additional Oxidative Hair Colorant ingredients pH

The oxidative hair colorant compositions of the present invention may have a pH of from 8 to 12, preferably from 8 to 10. For embodiments comprising a peroxymoncarbonate ion, the pH is preferably up to and including pH 9.5, more preferably from about 9.5 to about 7.5, even more preferably from about 9.5 to about 8.4, most preferably from about 9.4 to about 8.5, and even more preferably about pH 9.3 or 9.0.

Any sub-components of the oxidative hair colorant compositions, such as a tint composition or a developer composition may have a different pH from the oxidative hair colorant composition. For example, if the tint composition comprises an alkalizing agent, the tint composition will have an alkaline pH, such as higher than 8.

The pH of the compositions can be determined by using either a Mettler Toledo MP220 or a MP225 pH equipment, fitted with a standard laboratory pH electrode. The equipment is calibrated before each use using standard calibration buffers and using the standard calibration procedure.

Hair Dye

The oxidative hair colorant composition may contain a hair dye in addition to the 1,4-diamino-2-methoxymethyl benzene which may be selected from those known in the art, e.g. oxidative dye precursors, through which the coloring is produced by the action of oxidizing agents, such as for example hydrogen peroxide, or in the presence of atmospheric oxygen (if necessary with the addition of a suitable enzyme system). The hair dye may be an oxidative dye precursor, a direct dye, or a mixture thereof.

Oxidative Dye Precursors

The oxidative hair colorant compositions may include oxidative dye precursors in the form of primary intermediates or couplers. The precursors suitable for use, in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic hydroxyl groups, in the form of their salts with bases, such as alkali phenolates.

It is to be understood that the precursors detailed below are only by way of example and are not intended to limit the hair care compositions or sub-components such as tint compositions herein. These are: 1,7-dihydroxynaphthalene (INCI 1,7-naphthalenediol); 1,3-diaminobenzene (INCI m-phenylenediamine); 1-methyl-2,5-diaminobenzene (INCI toluene-2,5-diamine); 1,4-diaminobenzene (INCI p-phenylenediamine); 1,3-dihydroxybenzene (INCI resorcinol); 1,3-dihydroxy-4-chlorobenzene, (INCI 4-chlororesorcinol); 1-hydroxy-2-aminobenzene, (INCI o-aminophenol); 1-hydroxy-3-aminobenzene (INCI m-aminophenol); 1-hydroxy-4-aminobenzene (INCI p-aminophenol); 1-hydroxynaphthalene (INCI 1-naphthol); 1,4-dihydroxybenzene (INCI hydroquinone); 1-hydroxy-4-methylaminobenzene (INCI p-methylaminophenol); 1-methyl-2-hydroxy-4-aminobenzene (INCI 4-amino-2-hydroxy-toluene); 1-methyl-2-hydroxy-4-(2'-hydroxyethyl)aminobenzene (INCI 2-methyl-5-hydroxyethylamino-phenol); 1,2,4-trihydroxybenzene; 1-phenol-3-methylpyrazol-5-on (INCI phenylmethylpyrazolone); 1-(2'-hydroxyethyloxy)-2,4-diaminobenzene (INCI 2,4-diaminophenoxy-ethanol HCl); 1-hydroxy-3-amino-2,4-dichlorobenzene (INCI 3-amino-2,4-dichloro-phenol); 1,3-dihydroxy-2-methylbenzene (INCI 2-methylresorcinol); 1-amino-4-bis-(2'-hydroxyethyl)aminobenzene (INCI N,N-bis-(2-hydroxy-ethyl)-p-phenylene-diamine); 2,4,5,6-tetraminopyrimidine (INCI HC Red 16); 1-hydroxy-3-methyl-4-aminobenzene (INCI 4-amino-m-cresol); 1-hydroxy-2-amino-5-methylbenzene (INCI 6-amino-m-cresol); 1-(2'-hydroxyethyl)-2,5-diaminobenzene (INCI hydroxyethyl-p-phenylene diamine sulfate); 1-methoxy-2-amino-4-(2'-hydroxyethylamino)benzene, (INCI 2-amino-4-hydroxyethylaminoanisole); 1-hydroxy-2-amino-6-methylbenzene (INCI 6-amino-o-cresol); 1-(2'-hydroxyethyl)-amino-3,4-methylenedioxybenzene (INCI hydroxyethyl-3,4-methylenedioxy-aniline HCl); 3,5-diamino-2,6-dimethoxypyridine (INCI 2,6-dimethoxy-3,5-pyridinediamine); 5,6-dihydroxyindole (INCI 5,6-dihydroxyindole); 4-amino-2-aminomethylphenol (INCI 2-aminoethyl-p-amino-phenol HCl); 2,4-diamino-5-methylphenetol (INCI 2,4-diamino-5-methyl-phenetole HCl); 2,4-diamino-5-(2'-hydroxyethyloxy)toluene (INCI 2,4-diamino-5-methylphenoxyethanol HCl); 1,3-bis(N-(2-hydroxyethyl)-N-(4-amino-phenyl)amino)-2-propanol (INCI hydroxypropyl-bis-(N-hydroxy-ethyl-p-phenylenediamine) HCl); 3-amino-2-methylamino-6-methoxypyridine (INCI HC Blue No. 7); 1-phenyl-3-methyl-5-pyrazolone (INCI 2,4-dihydro-5-methyl-2-phenyl-3H-pyrazol-3-one); 2-amino-3-hydroxypyridine (INCI 2-amino-3-hydroxypyridine); 5-amino-salicylic acid; 4-hydroxy-2,5,6-triaminopyrimidine (INCI 2,5,6-triamino-4-pyrimidinol sulfate); 2,2'-[1,2-ethanediyl-bis-(oxy-2,1-ethanediyloxy)]-bis-benzene-1,4-diamine (INCI PEG-3,2',2'-di-p-phenylenediamine); 5,6-dihydroxyindoline (INCI dihydroxyindoline); N,N-dimethyl-3-ureidoaniline (INCI m-dimethyl-amino-phenylurea); 2,4-diamino-5-fluorotoluenesulfatehydrate (INCI 4-fluoro-6-methyl-m-phenylenediamine sulfate); 1-acetoxy-2-methylnaphthalene (INCI 1-hydroxyyethyl-4,5-diaminopyrazole sulfate); 1-acetoxy-2-methylnaphthalene (INCI 2-methyl-1-naphthol); 2-amino-5-ethylphenol (INCI 2-amino-5-ethylphenol); and p-anilinoaniline (INCI N-phenyl-p-phenylenediamine), 1-(3-aminophenyl)urea, 1-hydroxyethyl-4,5-diaminopyrazole sulfate, 2-(1,2-dihydroxyethyl)-p-phenylenediamine, 2-(2,5-diamino-4-methoxyphenyl)propane-1,3-diol, 2-(7-amino-2H-benzo[b][1,4]oxazin-4(3H)-yl)ethanol, 2-(benzo[d][1,3]dioxol-5-ylamino)ethanol, 2,2'-(2-(4-aminophenylamino) ethylazanediyl)diethanol, 2,2'-(4,6-diamino-1,3-phenylene) bis(oxy)diethanol, 2,2'-methylenebis-4-aminophenol, 2,3-diamino-6,7-dihydropyrazolo[1,2-a]pyrazol-1(5H)-one dimethosulfonate, 2,4-dimethylbenzene-1,3-diol, 2,5,6-triamino-4-pyrimidinol, 2,6-diaminopyridine, 2-amino-5-phenylphenol, 2-chloro-p-phenylenediamine, 2-chlororesorcinol, 2-hydroxyethyl-p-phenylenediamine, 2-methoxymethyl-p-phenylenediamine, 2-methoxy-p-phenylenediamine, 2-methyl-5-hydroxyethylaminophenol, 3-(pyrrolidin-1-yl)aniline, 3-amino-2,6-dimethylphenol, 3-methyl-1-phenyl-1H-pyrazol-5 (4H)-one, 4,5-diamino-1-benzylpyrazole, 4,5-diamino-1-butylpyrazole, 4,5-diamino-1-ethylpyrazole, 4,5-diamino-1-isopropylpyrazole, 4,5-diamino-1-methylpyrazole, 4,5-diamino-1-pentylpyrazole, 4,6-dichlorobenzene-1,3-diol, 4-chloro-2-methylnaphthalen-1-ol, 4-methoxy-2-methylnaphthalen-1-ol, 5-Aminosalicylic acid, 5-methyl-2-(methylamino)phenol, hydroxypropyl-bis-(N-hydroxyethyl-p-phenylenediamine), N,N-bis(2-hydroxyethyl)-p-phenylenediamine and pyridine-2,6-diol.

Suitable examples of combinations of 1,4-diamino-2-methoxymethyl benzene and other dye precursors may be found in CA 2576189, Table 1.

Preferred oxidative dye precursors are 1,3-Dihydroxybenzene, 1,3-Dihydroxy-2-methylbenzene, 1-Hydroxy-3-aminobenzene, N,N-bis(2-hydroxyethyl)-p-phenylenediamine, and 2-Methyl-5-Hydroxyethylaminophenol and mixtures thereof.

The oxidative hair colorant composition or the tint composition may comprise from about 0.001 wt % to about 10 wt % of oxidative dye precursors other than 4-diamino-2-methoxymethyl benzene. The total quantity of the oxidative dye precursors contained in tint composition is up to about 12 percent by weight, especially from about 0.05% to about 6% by weight of the tint composition.

Direct Dyes

The inventive compositions may also comprise compatible direct dyes, in an amount sufficient to provide coloring, particularly with regard to intensity. Typically, such an amount will range from about 0.05% to about 4%, by weight of the tint composition. Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4, Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide, Disperse Dyes such as Disperse Red 17, Disperse Violet 1, Disperse Red 15, Disperse Violet 1, Disperse Black 9, Disperse Blue 3, Disperse Blue 23, Disperse Blue 377, Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1,2-(4-amino- 2-chloro-5-nitrophenylamino)ethanol, HC Red No. 3,4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9,2-chloro-6-(ethylamino)-4-nitrophenol, 6-nitropyridine-2,5-diamine, HC Violet No. 2,2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14, and Natural dyes such as Annato, Anthocyanin, Beetroot, Carotene, Capsanthin, Lycopene, Chlorophyll, Henna, Indigo, Cochineal and mixtures thereof.

To obtain specific color shades, moreover, additional conventional natural and/or synthetic direct dyes can be contained in the colorant, for example plant pigments such as henna or indigo, triphenylmethane dyes, aromatic nitro dyes, azo dyes, quinone dyes, cationic dyes (Basic dyes) or anionic dyes (Acid dyes).

Chelants

Suitable chelants for use herein are carboxylic acids (in particular aminocarboxylic acids) and phosphonic acids (in particular aminophosphonic acids) and polyphosphoric acids (e.g., linear polyphosphoric acids), including the salts and derivatives of these chelants.

Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996).

When related to chelants, the terms "salts and derivatives thereof" mean all salts and derivatives comprising the same functional structure as the chelant they are referring to and that have similar or better chelating properties. These terms include alkali metal, alkaline earth, ammonium, substituted ammonium salts (e.g., monoethanolammonium, diethanolammonium, triethanolammonium), esters of chelants having an acidic moiety and mixtures thereof, in particular all sodium, potassium or ammonium salts. The term "derivatives" also includes "chelating surfactant" compounds (these are chelants modified to bear a surfactant moiety while keeping the same chelating functionality). The term "derivatives" also includes large molecules comprising one or more chelating groups having the same functional structure as the parent chelants. An example of these large molecules is polymeric EDDS (ethylenediaminedisuccinic acid).

According to the present invention, the colorant compositions (mixture of dyeing composition and oxidizing composition) comprise from about 0.01% to about 5%, in some embodiments, from about 0.25% to about 3%, in certain embodiments, from about 0.5% to about 1% of chelant, salts thereof, derivatives thereof, or mixtures thereof.

Generally, the chelants of the invention do not penetrate the hair to any significant extent under typical oxidative hair-coloring conditions, thereby not affecting color formation inside the hair.

In certain embodiments, the chelant is negatively charged. A negatively charged chelant does not penetrate hair fibers. *Diffusion and Distribution of Element-Labelled Surfactants in Human Hair* Int. J. Cos. Sci. 26 p. 61-69 (2004).

Aminocarboxylic Acid Chelants

Aminocarboxylic acid chelants as defined herein are chelants having at least one carboxylic acid moiety (—COOH) and at least one nitrogen atom. Examples of aminocarboxylic acid chelants suitable for use herein include diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), EDDHA (ethylenediamine-N—N'-bis(ortho-hydroxyphenyl acetic acid)), diaminoalkyldi(sulfosuccinic acids) (DDS), N,N'-bis(2-hydroxybenzyl)ethylenediamine-N,N'-diacetic acid (HBED), salts thereof and derivatives thereof.

Other suitable aminocarboxylic type chelants for use herein are iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, salts thereof and derivatives thereof. Dipicolinic acid and 2-phosphonobutane-1,2,4-tricarboxylic acid are also suitable. Preferred for use herein is ethylenediamine-N,N'-disuccinic acid (EDDS), derivatives and salts thereof.

Amino-Phosphonic Acid Chelants

According to the present invention, the dyeing compositions may comprise a chelant selected from amino-phosphonic acid type chelants, salts thereof, derivatives thereof and mixtures thereof. Amino-phosphonic acid type chelants are defined as chelants comprising an amino-phosphonic acid moiety (—PO$_3$H$_2$) or its derivative —PO$_3$R$_2$ wherein R$_2$ is a C$_1$ to C$_6$ alkyl or aryl radical.

Suitable amino-phosphonic acid type chelants for use herein are aminotri-(1-ethylphosphonic acid), ethylenediaminetetra-(1-ethylphosphonic acid), aminotri-(1-propylphosphonic acid), and aminotri-(isopropylphosphonic acid). Preferred chelants for use herein are aminotri-(methylenephosphonic acid), ethylene-diamine-tetra-(methylenephosphonic acid) (EDTMP) and diethylene-triamine-penta-(methylenephosphonic acid) (DTPMP) and mixtures thereof.

Other Chelants

Examples of other chelants suitable for use herein include but are not limited to quercetin polyethyleneimines, polyphosphoric acid chelants, etidronic acid, Methylglycine diacetic acid, N-(2-hydroxyethyl)iminodiacetic acid, Iminodisuccinnic acid, N,N-Dicarboxymethyl-L-glutamic acid and N-lauroyl-N,N',N"-ethylenediamine diacetic acid.

In certain embodiments, the dyeing compositions of the invention comprise diethylenetriamine pentaacetic acid (DTPA), ethylenediamine-N,N'-disuccinic acid (EDDS), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), diethylene-triamine-penta-(methylenephosphonic acid) (DTPMP), salts thereof, derivatives thereof, or mixtures thereof. In further embodiments, the dyeing compositions of the invention comprise from about 0.1% to about 5% of diethylene-triamine-penta-(methylenephosphonic acid) and from about 0.1% to about 5% of ethylenediamine-N,N'-disuccinic acid And from about 0.1% to about 5% of diethylenetriamine pentaacetic acid.

Radical Scavenger

The tint compositions may further comprise a source of radical scavenger. As used herein the term radical scavenger refers to a species that can react with a carbonate radical to convert the carbonate radical by a series of fast reactions to a less reactive species, i.e. a carbonate radical scavenger.

Suitable radical scavengers for use herein may be selected from the classes of alkanolamines, amino sugars, amino acids, esters of amino acids and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof. Especially preferred compounds are glycine, sarcosine, lysine, serine, 2 methoxyethylamine, glucosamine, glutamic acid, morpholine, piperidine, ethylamine, 3 amino-1-propanol and mixtures thereof.

The compositions of the present invention may comprise from about 0.1% to about 10% by weight, preferably from about 1% to about 7% by weight of the tint composition of a radical scavenger.

Conditioning Agent

The oxidative hair colorant composition may comprise a conditioning agent although the conditioning agent would need to be carefully selected to not inhibit foam formation or stabilization, including premature foam collapse. Optionally, a separate conditioning composition comprising a conditioning agent may be used with the oxidative hair colorant product. Conditioning agents suitable are selected from silicone materials, amino silicones, fatty alcohols, polymeric resins, polyol carboxylic acid esters, cationic polymers, insoluble oils and oil derived materials and mixtures thereof. Additional materials include mineral oils and other oils such as glycerin and sorbitol. Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain.

Silicones can be selected from polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain or mixtures thereof. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion.

The conditioning agent will generally be used at levels of from about 0.05% to about 20% by weight of the conditioning composition, such as from about 0.1% to about 15%, such as of from about 0.2% to about 10%, such as from about 0.2% to about 2% by weight of the conditioning composition.

Oxidative Hair Colorant Product

The oxidative hair colorant product comprises a manually-actuable, non-aerosol dispenser equipped with a reservoir comprising a reservoir volume, a mixing chamber and a dispensing head. The reservoir may contain an oxidative hair colorant composition such that when the manually-actuable, non-aerosol dispenser is actuated, the oxidative hair colorant composition is mixed with air and the oxidative hair colorant composition is dispensed as a foam.

Manually-actuable, non-aerosol dispensers for foam generation are well known in the art. These foam dispensers comprise a reservoir for holding a liquid to be dispensed in the form of foam with an assembly which can be mounted on or in an opening of the reservoir. The assembly comprises a dip tube which extends into the reservoir and then into a mixing chamber, a liquid pump for pumping the liquid from the reservoir and an air pump to mix air with the liquid in the mixing chamber in order to form foam. The foam is dispensed out of the mixing chamber and through a dispensing channel out of a dispensing head comprising a dispensing orifice. In the dispensing channel one or more porous elements such as sieves or screens that may be arranged to form homogeneous foam.

Suitable manually-actuable, non-aerosol dispenser structure include the dimensions of the dip tube, dimensions of the air ingress into the mixing chamber, mixing chamber dimensions, including the ingress and egress orifices from the mixing chamber, dispensing channel dimensions, porous elements (such as screens or meshes) and dispensing head orifice.

The manually-actuable, non-aerosol dispenser may be a pump or squeeze foamers. Suitable examples of pump foamers are exemplified in EP 0613728 B1, WO 97/013585 A1 and EP 1716933 A1. Suitable squeeze foamers are exemplified by the following patents: U.S. Pat. Nos. 3,709,437; 3,937,364; 4,022,351; 4,147,306; 4,184,615; 4,615,467; and FR 2,604,622. One particular example of a squeeze foamer useful herein is a squeeze foamer that is able to dispense from an upright or inverted position such as the one discussed in U.S. Pat. No. 6,604,693 assigned to Taplast, and more specifically, at column 2, line 65, through column 4, line 67 of that patent.

The manually-actuable, non-aerosol dispenser comprises a reservoir. The reservoir comprises a volume such that the reservoir volume is larger than the volume of the hair colorant composition contained within the reservoir. The area of the reservoir that is not occupied by the hair colorant composition is the head space. The head space should remain relatively free of the hair colorant composition or bubbles of the hair colorant composition. If the reservoir is shaken or inverted while the hair colorant composition is contained therein, the head space should remain relatively free of the hair colorant composition or bubbles thereof. As used in this paragraph, "relatively free" means less than 50%, such as less than 75%, such as less than 90%, such as 75% to 100% of the head space volume is free from the hair colorant composition or bubbles thereof.

The reservoir is selected to have enough volume to contain the hair colorant composition, any part of the mechanism for foaming the hair colorant composition (such as a dip tube) and still have head space. The reservoir volume in one embodiment is selected to be from about 100 mL to about 500 mL, from about 150 mL to about 400 mL, such as 250 mL. The ratio of the reservoir volume to hair colorant composition volume is from about 0.30 to about 0.70, such as from about 0.40 to about 0.55.

The shape of the reservoir may be selected such that when the hair colorant composition is contained within the reservoir, the force required per volume displacement may be optimized. In one embodiment, the force required per volume displacement is optimized when the shape of the bottle is selected to have an elliptical cross-section as viewed from vertical axis of the bottle (from the top or bottom of the bottle). The elliptical cross-section is preferably concentric such that a neck suitable for a threaded or snap-on cap may be used to close the reservoir. The major axis of the elliptical cross-section is orientated such that it is perpendicular to the force applied to the reservoir surface FIG. 1 illustrates a general structure for a hair colorant composition product (25) comprising a foamer assembly (1) and a reservoir (3).

The reservoir (3) having a reservoir volume (27) that contains the hair colorant composition is fluidly connected to the mixing chamber (5) such that the hair colorant composition is transported from the reservoir (3) when the manually-actuable, non-aerosol dispenser (25) is dispensed (e.g., "stroke"). The fluid connection is a dip tube (7). The dip tube (7) diameter for the hair colorant composition having a relatively higher viscosity requires a relatively larger diameter in order to allow for easy dispensing (low amount of force needed to dispense) and to achieve the desired foam specific volume.

The dip tube (7) diameter is preferably selected to have a diameter of greater than 2.0 mm, preferably from about 2.0 mm to about 10.0 mm, more preferably from about 2.0 mm to about 7.0 mm, even more preferably between about 2.0 mm to about 6.0 mm and most preferably between about 3.0 mm and about 5.0 mm. The viscosity of the liquid with a dip tube (7) diameter between about 2.0 mm and about 8.0 mm allows for the liquid to be conveyed from the reservoir (3) into the mixing chamber (5) with lower amounts of force by the user during dispensing (e.g., "stroke") while achieving the desired foam density discussed herein.

The mixing chamber (5) comprises at least one air ingress orifice (9), at least one liquid ingress orifice (11) and at least one mixing chamber egress orifice (13). The mixing chamber (5) further comprises an internal volume and an exterior wall, which defines the internal volume of the mixing chamber (5). The mixing chamber (5) allows for the combination of the hair colorant composition and air to begin the formation of the foamed hair colorant composition. Modification of the various orifice (9, 11, 13) areas (the two-dimensions of the indicating orifices that comprise part of the mixing chamber (5) exterior wall) can affect the foam specific density, particularly the correlation of the air ingress orifice (9) and the liquid ingress orifice (11) such that the liquid to air ratio is appropriate.

The air ingress orifice (9) is suitable to convey air that has entered into the headspace of the reservoir (3). The mixing chamber (5) may comprise more than one air ingress orifice (9). In one embodiment, the mixing chamber (5) comprises one air ingress orifice (9). The area of the air ingress orifice (9) may be from about 0.62 mm2 (about a 0.2 mm diameter circular air ingress orifice) to about 3.14 mm2 (about a 1 mm diameter circular air ingress orifice), preferably from about 1.26 mm2 (about a 0.4 mm diameter circular air ingress orifice) to about 1.88 mm2 (about a 0.8 mm diameter circular air ingress orifice). If more than one air ingress orifice (9) is selected, the total area of all air ingress orifices (9) should be used. Communication of the air in to the mixing chamber (5) via the air ingress orifice (9) can be and indirect communication with the mixing chamber (5) or a direct communication with the mixing chamber (5).

Similarly, the liquid ingress orifice (11) is suitable to fluidly convey the hair colorant composition into the mixing chamber (5) from the reservoir (3), preferably via a dip tube (7). In one embodiment, the mixing chamber (5) comprises more than one liquid ingress orifice (11). In one embodiment, the mixing chamber (5) comprises three liquid ingress orifices (11). The area of the liquid ingress orifice (11) should be from about 1.5 mm2 to about 3 mm2. In one embodiment the liquid ingress orifice (11) should be from about 1.8 mm2 to about 2.3 mm2. If more than one liquid ingress orifice (9) is selected, the total area of all air ingress orifices (9) should be used. For example, a total area of 2.0 mm2 for three liquid ingress orifices (11) would equate the total areas of all three liquid ingress orifices (11) combined. The fluid conveyance from the reservoir (3) to the mixing chamber (5) may be an indirect communication pathway with the mixing chamber (5) or a direct communication pathway with the mixing chamber (5).

As used herein "indirect communication" means that the conveyance of the air or hair colorant composition to the mixing chamber (5) travels along a pathway through some other physical structure before entering into the mixing chamber (5). For example, the air or hair colorant composition will come into contact with the exterior wall of the mixing chamber (5) before entering into the mixing chamber (5) through the respective orifice (9, 11). In one embodiment, a void volume (30) is contiguous with the exterior wall of the mixing chamber (5). The air or the hair colorant composition is conveyed from the reservoir, through the dip tube (7) into the void volume (30) external to the mixing chamber (5). The void volume (30) is in air and/or in liquid communication with the air ingress orifice (9) and/or the liquid ingress orifice (11), respectively.

As used herein "direct communication" means that the conveyance of the air or hair colorant composition to the mixing chamber (5) travels directly into the mixing chamber (5). For example, the air or hair colorant composition will come into contact with the internal volume of the mixing chamber (5) through the respective orifice (9, 11) without contacting a component exterior to the mixing chamber (5).

In one embodiment, the mixing chamber egress orifice (13) is selected to create an increase in pressure within the mixing chamber (5). The mixing chamber (5) may comprise more than one mixing chamber orifice (13). In one embodiment, the mixing chamber (5) comprises one mixing chamber egress orifice (13).

The mixing chamber (5) has an outer wall creating an internal volume of the mixing chamber (5). The top edge of the outer wall defines a circumference. The mixing chamber egress orifice (13) may be the same size area of the circumference of the mixing chamber (5) top edge, but preferably is selected to be smaller area than the area of the circumference of the mixing chamber (5) top edge so as to create an increase in pressure in the mixing chamber (5). The area of the mixing chamber egress orifice (13) may be between about 0.314 mm2 (0.1 mm diameter circular orifice) to about 9.42 mm2 (3 mm diameter circular orifice). In one embodiment, the mixing chamber egress orifice (13) comprises an area of about 2.512 mm2 (0.8 mm diameter circular orifice) to about 5.652 mm2 (1.8 mm diameter circular orifice). If more than one mixing chamber egress orifice (13) is present, the total area of all of the mixing chamber egress orifices should be considered.

In an embodiment, a diffuser plate (29) comprises the mixing chamber egress orifice (13). The diffuser plate (29) may be part of the mixing chamber (5) structure or it may be a separate component that fits into the mixing chamber (5).

The mixing chamber (5) is fluidly connected to the foamer assembly (1). The hair colorant composition enters into the mixing chamber (5) via the liquid ingress orifice (11) and mixes with air which enters the mixing chamber (5) via the air ingress orifice (9).

Air enters the manually-actuable, non-aerosol dispenser (25) after a stroke into the headspace of the reservoir (3). The controlled entry or exit of air into the manually-actuable, non-aerosol dispenser (25) reservoir (3) headspace may be accomplished by a ball valve (23) or silicone seal or gasket. The ball valve or silicone seal or gasket may be located in the foamer assembly (1) an in communication with the headspace. In one embodiment, the ball valve (23), silicone seal or gasket is located to communicate between the reservoir (3) and the air external to the manually-actuable, non-aerosol dispenser (25) such that when the manually-actuable, non-aerosol dispenser (25) is being dispensed, the ball valve (23) silicone seal or gasket excludes entry of air external to the manually-actuable, non-aerosol dispenser (25) into the reservoir (3) headspace so that the air in the headspace is conveyed to the mixing chamber through the air ingress orifice (9). After dispensing ("stroke"), the ball valve (23), silicone seal or gasket allows entry of air external to manually-actuable, non-aerosol dispenser (25) to enter into the reservoir (3) to refill the headspace for the next stroke.

After the hair colorant composition and air enter into the mixing chamber (5) and form the foamed hair colorant composition, the foamed hair colorant composition exits the mixing chamber (5) via the mixing chamber egress orifice (13), traveling through a foam fluid connection (17) to the foamer assembly (1) and exits the foamer dispensing orifice (19). The foam fluid connection (17) between the mixing chamber egress orifice (13) and the foamer dispensing orifice (19) may have present therein one or more screens or meshes (21a, 21b, 21c) which may be used to modify the foam specific volume. The number of meshes, the size of the openings in the meshes and the frequency of the openings in the meshes may be used to modify the foam specific volume. The meshes may have opening size is from about 70 micron ($\mu$) to about 170 micron ($\mu$), preferably from about 50 microns ($\mu$) to about 350 micron ($\mu$), more preferably from 70 micron ($\mu$), to about 300 micron ($\mu$), most preferably from about 70 micron ($\mu$) to about 270 micron ($\mu$). In one embodiment, at least 2 meshes (21a, 21b) are utilized, wherein the 2 meshes (21a, 21b) are contiguous with each other. The meshes comprise a diameter section and a depth. The diameter section (largest surface area of the mesh) is the portion of the mesh which would be contiguous with another mesh.

At least a lower portion of the dip tube (7) may be angled toward a lowermost front corner of the reservoir (3) when the reservoir (3) is tilted at an angle for optimal squeezing and dispensing of foam, so as to maximize efficient use of the hair colorant composition in the reservoir (3). The angle of incline of the lowermost portion of the dip tube (7) preferably mimics the angle of incline of the foamer dispensing orifice (19), and both are preferably at an angle downward from a horizontal axis through the mesh closest to the dispensing head orifice (19) in a range of about 30° to about 45°.

In one embodiment, one to three meshes are present in the fluid connection between the mixing chamber egress and the dispensing head orifice. In one embodiment, two meshes (21a, 21b) are located in the foam fluid connection (17) in close proximity to the mixing chamber egress orifice (13), wherein the two meshes (21a, 21b) comprise about 170 micron ($\mu$) opening size and wherein one mesh (21c) is located in close proximity to the foamer dispensing orifice (19), wherein the one mesh (21c) comprises about a 70 micron ($\mu$) opening size.

In one embodiment two meshes (21a, 21b) located in the foam fluid connection (17) in close proximity to the mixing chamber egress orifice (13) and the two meshes (21a, 21b) are contiguous with each other, wherein the two meshes (21a, 21b) comprise about 170 micron ($\mu$) opening size and wherein one mesh (21c) is located in close proximity to the foamer dispensing orifice (19), wherein the one mesh (21c) comprises about a 70 micron ($\mu$) opening size. Each mesh is preferably provided as an injection molded wafer or disc having a cylindrical sidewall and a screen extending across one end of the cylindrical sidewall. The screen does not extend axially (from the top edge of the cylindrical sidewall to the bottom edge of the cylindrical sidewall moving along the y-axis) the entire length of the cylindrical sidewall. As used in this paragraph, "contiguous" means that the two cylindrical sidewalls of the respective wafers or discs are immediately adjacent one another. However, each of the respective wafers is preferably oriented with its screen is facing up, such that even with the two wafers or discs in contact with one another, there is a gap separating the screen of the first disc from the screen of the second disc.

Figure 3:
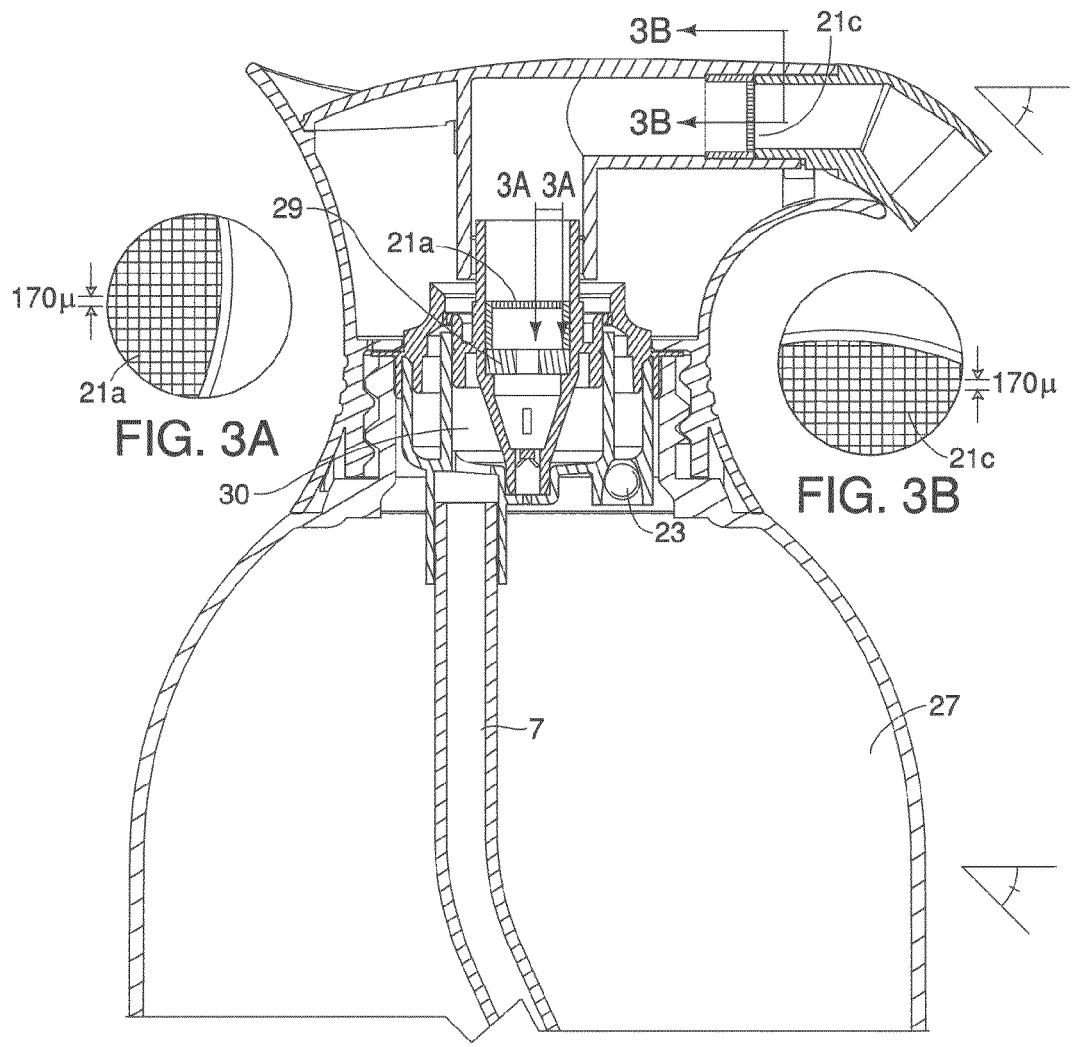
FIG. 3 is a cross-sectional view of an alternate embodiment of the manually-actuable, non-aerosol dispenser of the present disclosure.
Figure 4:
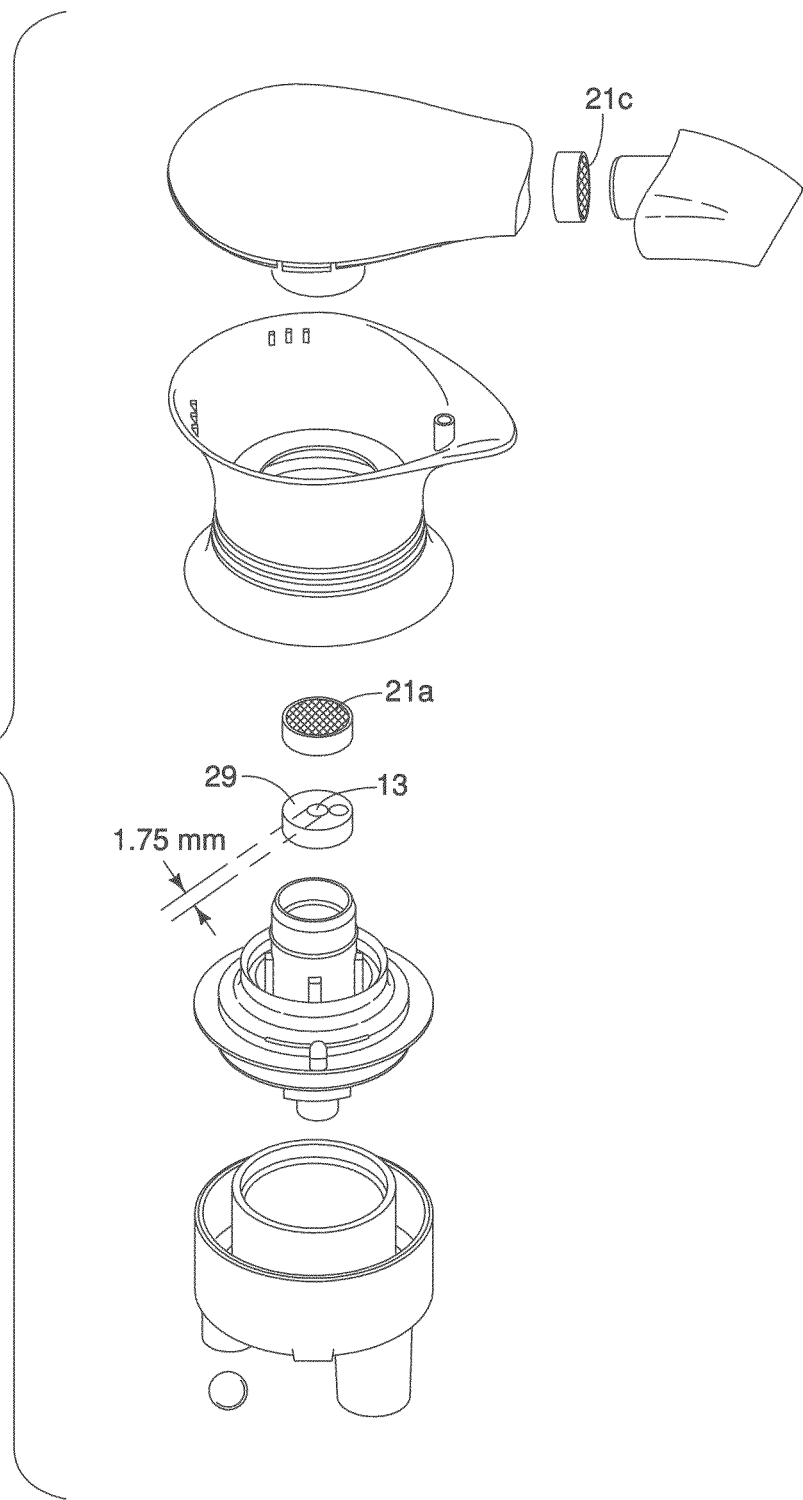
FIG. 4 is an exploded view of a dispenser head of the dispenser of FIG. 3.

Turning now to FIG. 3, a particularly preferred embodiment is illustrated in which only two meshes (21a, 21c) are utilized, one (21a) in close proximity to the mixing chamber egress orifice (13) and the other (21c) disposed close proximity to the foamer dispensing orifice (19).

By varying the size of the mixing chamber egress orifice (13), the number of meshes (21a, 21b, 21c), and the opening size of the screens of the meshes, it is possible to reduce the amount of work required to expel a desired quantity of foam, while substantially preserving the desired foam specific volume. For instance, in an exemplary implementation of the embodiment illustrated in FIG. 1, a mixing chamber egress orifice (13) of 1 mm diameter is provided in a diffuser plate (29) [area of orifice is pi*diameter]. In that embodiment, three mesh wafers or discs are provided in the foam fluid connection (17), with each of the first two (21a, 21b) comprising a mesh opening size of about 170 micron ($\mu$), and the third comprising a mesh opening size of about 70 micron ($\mu$). The squeeze is ultimately completed when a sufficient quantity of product is dispensed into the hand for a single application onto the desired surface, such as hair to be treated with a colorant. Alternatively, the squeeze may be held until one or both of the ergonomics of the displaced (i.e., indented) bottle or reservoir, and the hold time at the maximum force, dictate to the user that another squeeze is needed.

In an exemplary implementation of the embodiment illustrated in FIG. 3, the second mesh (21b) is omitted, the mixing chamber egress orifice is increased to 1.75 mm in a diffuser plate (29) [area of orifice is pi*diameter], the first mesh (21a) has a mesh opening size of about 170 micron ($\mu$), and the mesh wafer or disc (21c) comprises a mesh opening size of about 70 micron ($\mu$) in located in the foam fluid connection (17).

Kits

Oxidative hair colorant products are often sold as a kit containing individually packaged subcomponents such as a tint composition component, a developer composition component and a alkaline composition component that are packaged with gloves and instructions in a box. Optionally a conditioning composition component is also included. A user will combine the subcomponents, such as the tint composition component and the developer composition component, foaming the resulting mixed composition (oxidative hair coloring composition) in the manually-actuable, non-aerosol dispenser and then applying the mixed composition in the form of foam to the desired hair surface.

Included in the kit of the present application is manually-actuable, non-aerosol dispenser. The dispenser is capable of dispending the oxidative hair colorant composition in a foam.

The kit may contain two or more containers. In one embodiment, the tint composition component is contained in one container and the developer composition component is contained in the manually-actuable, non-aerosol dispenser. In another embodiment, the tint composition component is contained in one container, an alkalizing component is contained is a second container and the developer composition component is contained in the manually-actuable, non-aerosol dispenser.

Optional components for the kit include a conditioner composition and a refreshing color composition. The conditioner composition may comprise a conditioning agent. The refreshing color composition may comprise a conditioning agent and direct dyes.

Figure 5:
FIG. 5 is an embodiment of a kit containing the manually-actuable, non-aerosol dispenser containing a developer composition, a tint composition in a separate bottle, a conditioning composition in a separate sachet, gloves and instructions.

FIG. 5 shows one embodiment of the kit comprising a box (50), instructions (52), gloves (54), a tint composition (56), a developer composition (58) in the reservoir (3), a foamer assembly (1) and a conditioner composition (60).

Method of Use

Hair coloring mixtures are usually sold in kits comprising, in individually packaged components such as separate containers. Generally, the weight ratio of tint composition:developer composition for a hair colorant composition is in the range 5:1 to 1:5, such as 1:1, 1:1.5, 1:2, 1:3 and 1.4 depending on strength of developer composition and tint composition.

A user mixes a tint composition and a developer composition together in the reservoir of the manually-actuable, non-aerosol dispenser immediately before use. If the optional subcomponent that is an alkalizing composition, such as one that contains monoethanolamine (MEA), then the kit would contain a separate container for the subcomponent. The three components may be mixed in a 1:1:1 weight ratio. The user mixes a tint composition, a alkalizing composition and a developer composition together in the reservoir of the manually-actuable, non-aerosol dispenser immediately before use.

The user may then shake to mix the tint composition and developer composition. Shaking may be in a vertically reciprocating motion or in a rotating reciprocating shaking motion for 3 to 5 times to mix the tint composition and developer composition. The user then actuates the manually-actuable, non-aerosol dispenser to dispense foam (foamed hair colorant composition) either into the user's gloved hand or directly onto the hair.

Application of the foamed hair colorant composition to the hair may be undertaken in several ways. Application of the foamed hair colorant composition may take place on the whole head of hair of an end user. As used herein, the "whole head of hair" means that the hair all over the head from the root of the hair to the tip of the hair is included in the application process. By contrast, the application of the foamed hair colorant composition may take place on the root portion of the hair. The application to the root portion of the hair may still be over the entire head of the end user, but application of the foamed hair colorant composition is applied only to the section of hair closest to the head (root portion), which is between about 0.01 mm to about 4 mm from the scalp of the head. Also, application may take place on a portion of hair. Application of a portion of hair is commonly referred to as highlighting or lowlighting. The portion of hair may be physically separated from the whole head of hair in a hair bundle or may be a smaller portion of hair than the whole head of hair. A hair bundle may be physically separated from a whole head of hair by a device including a plastic cap through which hair bundles are formed when hair is pulled through orifices in the plastic cap, metal foils encompassing a hair bundle, strand separators applied to hair at the root portion, or similar devices.

The dispenser preferably is equipped with a reservoir that includes a reservoir volume, a mixing chamber, a dispensing head, at least one mesh disposed intermediate a mixing chamber egress orifice of the mixing chamber and a dispenser head orifice of the dispensing head. Further, the dispenser includes a dip tube in fluid communication with the mixing chamber and the reservoir volume.

The dispensing of the foam can be carried out by squeezing the exterior of the reservoir of the manually-actuable, non-aerosol dispenser. Consistent therewith, the foam can be dispensed through the dispensing head orifice of the dispensing head.

A more specific method or process of coloring hair using the foamers of the present disclosure will now be described. A method of coloring hair with at least 100 grams of hair coloring foam, preferably about 110 g, and more preferably, 120 g, comprises the following steps:

(1) Creating a hair colorant composition by combining a developer composition and a tint composition in a manually-actuable, non-aerosol dispenser equipped with a reservoir comprising a reservoir volume, a mixing chamber, a dispensing head, at least one mesh disposed intermediate a mixing chamber egress orifice of the mixing chamber and a dispenser head orifice of the dispensing head, each of the at least one mesh having a screen opening size in the range of about 30 micron to about 170 micron, and a dip tube in fluid communication with the mixing chamber and the reservoir volume, the reservoir portion thereof being a squeezable container that, upon application and maintenance of a force from opposing directions, compresses and directs hair colorant composition within the reservoir into the dip tube.

(2) Mixing the tint composition and the developer composition to form the hair colorant composition by shaking the manually-actuable, non-aerosol dispenser. As used herein, shaking includes at least turning the manually-actuable, non-aerosol dispenser a plurality of times back and forth to form the hair colorant composition.

(3) Squeezing the exterior of the reservoir of the manually-actuable, non-aerosol dispenser, thereby dispensing the hair colorant composition from the reservoir in the form of a foamed hair colorant composition, so that the foam is expelled through the dispensing head orifice.

(4) Applying the foamed hair colorant composition to hair to be colored.

(5) Repeating steps (2) and (3) a plurality of times, the plurality of times to be no more than 60 times, preferably no more than 50 times, and more preferably, no more than 45 times.

(6) Permitting the foamed hair colorant composition applied to the hair to react with the hair for a predetermined time, the predetermined time being commensurate with the time it takes for the hair to reach the color which the oxidative hair colorant composition is formulated to achieve, and the predetermined period of time preferably not exceeding 40 minutes, such as between 10 and 30 minutes.

(7) Rinsing the hair to which the foamed hair colorant composition was applied with water to remove any remaining hair colorant composition.

The method may include an optional additional step (8) of treating the hair and scalp with a post-colorant care composition.

In one embodiment, the foamed hair colorant composition collapses to a liquid and remains on the hair for 5 to 30 minutes (to ensure uniform application to all of the hair), the consumer then rinses his/her hair thoroughly with water and allows it to dry.

When present, the optional conditioning agent can be provided in a third container. In one embodiment, the content of the third container can be applied (after an optional rinse step) as a post-treatment immediately after the hair colorant composition.

According to the present invention the methods of coloring hair also comprise embodiments whereby the composition of the present invention is applied to the hair and preferably the mixture is worked for a few minutes (to ensure uniform application to all of the hair). The composition is then allowed to remain on the hair in order for the color to develop for a time period of less than about 20 minutes, preferably less than about 15 minutes, more preferably from about 5 minutes to about 10 minutes, most preferably for about 10 minutes. The consumer then rinses his/her hair thoroughly with tap water and allows it to dry and or styles the hair as usual.

According to a further alternative embodiment of the present invention, the method of coloring the hair is a sequential hair coloring method comprising the steps of at least two sequential hair color treatments wherein the time period between each treatment is from 1 to 60 days, preferably from 1 to 40 days, more preferably from 1 to 28 days, even more preferably from 1 to 14 days and most preferably from 1 to 7 days. In such embodiments the time that the composition is retained on head may be less than about 20 minutes and is preferably less than about 10 minutes and most preferably from about 2 minutes to about 5 minutes.

Test Methods
Viscosity
Sample Preparation

The tint composition and developer composition (and optional alkalizing composition) are combined to make an oxidative hair colorant composition. The sample preparation of the oxidative hair colorant composition should be as follows:

1. Mixing is achieved by means of a SpeedMixer, Model 400 DAC FVZ or equivalent device. SpeedMixers and suitable mixing cups are available from The FlackTek Company, Landrum, S.C. The developer composition and the tint composition are equilibrated at 25.0° C. prior to mixing. A cylindrical translucent polypropylene cup having an internal diameter of about 6 cm and a depth of about 8.5 cm with a screw-on lid is used as a mixing container. A 60.0 gram aliquot of the developer composition is weighed into the container and a pre-weighed 60.0 gram aliquot of the tint composition is then added rapidly. The container is capped, and the compositions are immediately mixed at 1950 rpm for 30 seconds using the SpeedMixer.

2. The sample is then measured for viscosity.

Low Shear (Mixed) Viscosity and High Shear Viscosity

The viscosity of the mixture is measured using a TA Instruments AR 2000 Rheometer or equivalent device equipped with a Peltier plate and a stainless steel cone having a 40 mm diameter and a 2° angle. The instrument is calibrated according to the manufacturer's instructions and the Peltier plate is set at 25.0° C. The cone is raised to a position approximately 4.5 cm above the plate.

Immediately after the mixing step, 3.0 mL of the mixture is transferred gently onto the center of the Peltier plate using a disposable pipette with an internal tip diameter of approximately 3 mm Any bubbles are removed by drawing them into the pipette. The cone is lowered to obtain the specified gap between the tip of the cone and the upper surface of the Peltier plate. The gap setting is specified by the manufacturer of the cone and is typically approximately 60 microns. The rheometer is programmed to operate in rotational mode with the shear stress ramped from $6.0\times10^{-3}$ to 800 Pa over a period of 252 seconds. Rotation is initiated immediately after the specified gap is established. Viscosity data collected during the measurement period are plotted as a function of shear rate ($s^{-1}$). The low shear viscosity value (mixed viscosity) is the actual or interpolated viscosity at 10.0 $s^{-1}$ and the high shear viscosity value is the actual or interpolated viscosity at 500 $s^{-1}$.

Foam Specific Volume

Foam specific volume is measured by placing a 100 ml beaker onto a mass balance, tarring the mass of the beaker and then dispensing from a foaming dispenser into the 100 ml beaker until the volume of the foam is equal to 100 ml. Record the resulting mass of the 100 ml of foam at 5 seconds from the end of dispensing. Dividing the volume (100) by the mass of the foam results in the foam specific volume having the units of ml/g.

FORMULATION EXAMPLES

TABLE 1

| | Tint Compositions | | |
|---|---|---|---|
| | A | B | C |
| | | SHADE | |
| Component | Red<br>% by weight of<br>tint composition | Light Golden<br>Brown<br>% by weight of<br>tint composition | Black<br>% by weight of<br>tint composition |
| Ethoxydiglycol | 13.00 | 10.00 | 15.00 |
| Propylene glycol | 5.00 | 5.00 | 5.00 |
| Trisodium ethylenediamine disuccinate | 1.50 | 1.50 | 1.50 |
| Sodium Chloride | 1.25 | 1.20 | 0.50 |
| Sodium Hydroxide | 0.34 | 0.60 | — |
| Erythorbic Acid | 0.30 | 0.30 | 0.30 |
| Ethylene Diamine Tetraacetic Acid - EDTA | 0.10 | 0.10 | 0.10 |
| Sodium sulfite | 0.10 | 0.10 | 0.10 |
| Citric acid Anhydrous | 0.60 | 0.60 | 0.60 |
| Isopropyl Alcohol | 5.00 | 4.00 | 4.50 |

TABLE 1-continued

Tint Compositions

| Component | A<br>Red<br>% by weight of tint composition | B<br>Light Golden Brown<br>% by weight of tint composition | C<br>Black<br>% by weight of tint composition |
|---|---|---|---|
| | | SHADE | |
| Monoethanolamine | 5.50 | 5.50 | 4.50 |
| m-Aminophenol | — | 0.129 | — |
| 1-Naphthol | 0.100 | — | — |
| 1,4-Diamino-2-(methoxymethyl)-benzene | 1.500 | 0.686 | 3.000 |
| Resorcinol | — | 0.266 | 0.700 |
| P-Aminophenol | — | 0.683 | 0.400 |
| 2-Methylresorcinol | — | 0.547 | — |
| 4-Amino-2-Hydroxytoluene | 1.000 | 0.124 | — |
| 1-Hydroxyethyl 4,5-Diamino Pyrazole Sulfate | 1.500 | — | 0.060 |
| PHENYL METHYL PYRAZOLONE | 0.125 | 0.059 | — |
| 2-Methyl-5-Hydroxyethylaminophenol PAOX | 0.700 | — | — |
| 2-Amino-4-Hydroxyethylaminoanisole Sulfate | — | 0.025 | 0.900 |
| Hydroxyethyl-3,4-Methylenedioxyaniline HCl | — | — | 0.800 |
| Water | to 100% | to 100% | to 100% |

TABLE 2

Developer Composition

| Ingredient | A<br>% by weight of developer composition | B<br>% by weight of developer composition | C<br>% by weight of developer composition |
|---|---|---|---|
| Etidronic acid | 0.08 | 0.08 | 0.08 |
| Hydrogen peroxide (50% active) | 9.0 | 9.0 | 9.0 |
| ACULYN ® 33 | 7.0 | 5.0 | 2.0 |
| ACULYN ® 22 | 3.5 | 5.0 | 7.0 |
| Water | to 100% | to 100% | to 100% |

Each tint formulation may be admixed with the developer formulation to provide an oxidative hair colorant composition having the required high shear viscosity and low shear (mixed) viscosity. The weight ratio of tint formulation to developer formulation may be varied depending upon the precise shade required and the degree of bleaching necessary to attain the desired shade. Generally, the weight ratio of tint formulation:developer formulation is in the range 5:1 to 1:5, such as 1:1, 1:2 and 1:3 depending on strength of developer composition and composition of tint.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oxidative hair colorant product comprising:
    a. an oxidative hair colorant composition comprising:
        i) from about 0.1 wt % to about 10 wt % by weight of the oxidative hair colorant composition of a free-base of 1,4-diamino-2-methoxymethyl benzene;
        ii) an alkalizing agent;
        iii) a solvent;
        iv) an oxidizing agent;
        v) a foaming agent; and
        vi) a salt; and
    b. a manually-actuable, non-aerosol dispenser;
    wherein the oxidative hair colorant composition has a high shear viscosity of less than 200 mPa·s and a low shear (mixed) viscosity of between 10 mPa·s and 500 mPa·s.

2. The oxidative hair colorant product of claim 1 wherein the oxidative hair colorant composition further comprises from about 0.001 wt % to about 10 wt % by weight of the oxidative hair colorant composition of at least one oxidative dye precursor other than the free-base form of 1,4-diamino-2-methoxymethyl benzene.

3. The oxidative hair colorant product of claim 2 wherein the at least one oxidative dye precursor is selected from 1,3-Dihydroxybenzene, 1,3-Dihydroxy-2-methylbenzene, 1-Hydroxy-3-aminobenzene, N,N-bis(2-hydroxyethyl)-p-phenylenediamine, and 2-Methyl-5-Hydroxyethylaminophenol.

4. The oxidative hair colorant product of claim 1 wherein the oxidative hair colorant composition comprises from 0.1 to 30% by weight of a solvent.

5. The oxidative hair colorant product of claim 1 wherein the oxidative hair colorant composition comprises from about 0.1% to about 10% by weight of the alkalizing agent selected from alkanolamines, alkali-metal and ammonium hydroxides, alkali-metal and ammonium carbonates.

6. The oxidative hair colorant product of claim 1 wherein the oxidative hair colorant composition comprises from about 0.1% to about 40% by weight of an oxidizing agent and said oxidizing agent is selected from the group consisting of include hydrogen peroxide, inorganic alkali metal peroxides, urea peroxide, melamine peroxide, and alkali metal salts of perborates, percarbonates, perphosphates, persilicates, persulphates.

7. The oxidative hair colorant product of claim 1 wherein the oxidative hair colorant composition comprises from about 0.1 wt % to about 20 wt % by weight of a surfactant as the foaming agent.

8. The oxidative hair colorant product of claim 1 wherein the oxidative hair colorant composition comprises from about 4 to about 25% by weight of a polymeric foam stabilizer as the foaming agent.

9. The oxidative hair colorant product of claim 1 wherein the oxidative hair colorant composition comprises from about 0.1 wt % to about 10 wt % by weight of a surfactant and from about 4 to about 25% by weight of a polymeric foam stabilizer as the foaming agent.

10. The oxidative hair colorant composition of claim 8 wherein said foam stabilizing agent is a polymeric foam stabilizer selected from the group consisting of hydroxypropyl methylcellulose, methylcellulose, cecetyl hydroxyethylcellulose and mixtures thereof.

11. The oxidative hair colorant composition of claim 8 wherein said foam stabilizing agent is selected from the group consisting of:
 (1) an Acrylates/Steareth-20 Methacrylate Copolymer;
 (2) an Acrylates Copolymer; and
 (3) mixtures thereof.

12. The oxidative hair colorant composition of claim 8 wherein said foam stabilizing agent is an acrylate/$C_{10-30}$ alkyl acrylate crosspolymer.

13. The oxidative hair colorant composition of claim 8 wherein said foam stabilizing agent is selected as a polymer comprising vinyl pyrrolidone (VP), dimethylaminopropyl methacrylamide (DMAPA) and methacryoylaminopropyl lauryldimonium chloride (MAPLAC).

14. The oxidative hair colorant composition of claim 8 wherein said foam stabilizing agent is a polyethyleneoxide-polypropyleneoxide-polyethyleneoxide block polymer terminating in primary hydroxyl groups.

15. The oxidative hair colorant composition of claim 8 wherein said foam stabilizing agent is selected from the group consisting of polysaccharides, cellulosic materials, amine-bearing polymers, acidic polymers obtainable from natural sources, chemically modified starches, carboxyvinyl polymers, polyvinylpyrrolidone, polyvinyl alcohol, polyacrylic acid polymers, polymethacrylic acid polymers, polysiloxanes and mixtures thereof.

16. The oxidative hair colorant product of claim 1 wherein the oxidative hair colorant composition further comprises at least one direct dye.

17. An oxidative hair colorant composition comprising:
 i) from about 0.1 wt % to about 10 wt % by weight of the oxidative hair colorant composition of a free-base of 1,4-diamino-2-methoxymethyl benzene;
 ii) an alkalizing agent;
 iii) a solvent;
 iv) an oxidizing agent;
 v) a foaming agent; and
 vi) a salt;
wherein the oxidative hair colorant composition comprises a low shear (mixed) viscosity from about 50 mPa s to about 500 mPa·s; and a high shear viscosity of the oxidative hair colorant composition is less than 200 mPa·s.

18. A kit comprising components to form an oxidative hair colorant composition, the kit comprising:
 a tint composition component comprising a solvent, a free-base of 1,4-diamino-2-methoxymethyl benzene and at least one other dye precursor, a salt and an alkalizing agent;
 a developer composition component comprising an oxidizing agent; and
 a manually-actuable, non-aerosol dispenser.

* * * * *